United States Patent [19]

Top et al.

[11] Patent Number: 5,554,602
[45] Date of Patent: Sep. 10, 1996

[54] LABELLING OF HORMONES WITH RHENIUM AND TECNETIUM

[75] Inventors: Siden Top, Lisses; Anne Vessieres; G'erard Jaquen, L'Hay-Les-Roses, all of France; Jacques Quivy, Louvain-Laneuve, Belgium

[73] Assignee: LaRegion Wallone, Namur, Belgium

[21] Appl. No.: 45,124

[22] Filed: Apr. 12, 1993

[30] Foreign Application Priority Data

Apr. 10, 1992 [FR] France .................................. 92 04411

[51] Int. Cl.$^6$ .............................. C07J 1/00; A61K 31/565
[52] U.S. Cl. ........................ 424/1.45; 514/182; 552/618; 552/629; 552/630; 552/631
[58] Field of Search ...................... 552/618, 629, 552/630, 631; 514/182

[56] References Cited

U.S. PATENT DOCUMENTS

| | | | |
|---|---|---|---|
| 4,465,676 | 8/1984 | Hochberg | 424/1.45 |
| 4,466,952 | 8/1984 | Hadd | 424/1.45 |
| 4,659,517 | 4/1987 | Spicer et al. | 424/1.45 |
| 4,725,426 | 2/1988 | Hofmeiste et al. | 424/1.45 |
| 4,855,125 | 8/1989 | Baranczuk et al. | 424/1.45 |
| 5,427,766 | 6/1995 | Dowd | 424/1.45 |

FOREIGN PATENT DOCUMENTS

| | | |
|---|---|---|
| 0105785 | 4/1984 | European Pat. Off. |
| 0345153 | 12/1989 | European Pat. Off. |
| 0441491 | 8/1991 | European Pat. Off. |

OTHER PUBLICATIONS

S. Top et al., "Reactions of eq, eq-Re2(CO)8(MeCn)2 with Phenylacettlene and alpha-Ethynylestradiol. A New Synthesis of Acetylide Complexes", J. Organometallic Chem., vol. 414, No. 1, Aug. 13, 1991.

G. Jaouen et al., "Transition Metal Carbonyl Oestrogen Receptor Assay", Pure & Applied Chemistry, vol. 57, No. 12, Dec. 1985, London, GB, pp. 1865–1874.

S. Top et al., "Synthetic, Structural, and Reactivity Studies of Di-Rhenium Carbonyl Complexes of 17-alha-Ethynylestradiol & Phenylacetylene: . . .", Organometallics, vol. 11, No. 3, US, pp. 1201–1209 (1992).

*Primary Examiner*—Kimberly J. Prior
*Attorney, Agent, or Firm*—Foley & Lardner

[57] ABSTRACT

The disclosed invention is drawn to the organometallic oestrogen complex of formula (I):

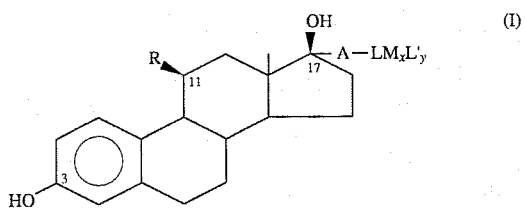

in which A is a $C_{1-7}$ alkylene radical or $C_{2-7}$ alkenylene or alkynylene radical; $M_x$ is one or more identical or different transition metals; $L'_y$ is one or more identical or different ligands complexing the metal(s) of $M_x$; and L is a ligand for covalently coupling $M_x$ to A; and R is H or a $C_{1-7}$ alkyl or alkoxy group which may be optionally substituted, particularly with one or more halogens. These complexes are useful for the treatment of hormone-dependent cancers. Also, when the metals of the complex $M_x$ are radioactive isotopes suitable for imaging, the complexes are useful as imaging agents.

13 Claims, No Drawings

LABELLING OF HORMONES WITH RHENIUM AND TECNETIUM

The present invention relates to new organometallic complexes of steroid hormones, especially oestrogen complexes. The present invention also relates to the use of the property of being a specific ligand for steroid hormone receptors, in particular oestrogen receptors, possessed by the complexes according to the invention, for application as imaging agents when they contain a radioactive isotope suitable for imaging, or use as a medicinal product, especially for the treatment of hormone-dependent cancers. In the latter case, when the metal is a suitable radioactive isotope, the complexes may be used in the context of the concept of targeted in situ radiotherapy.

Steroid hormones bind with a high affinity to the protein receptors located, in the case of oestrogens, in the nucleus of the target cells. After binding of the hormone, an activation phenomenon takes place which makes them capable of binding to the DNA and triggers activation of the transcription of the portions of the genome which control the physiological activity distinctive to the hormone. In view of the fact that the steroid-receptor complex comes in proximity to the DNA, a radioactive isotope carried by the steroid may seriously damage the DNA and have a lethal effect on the target cell.

Now, a number of cancers possess a high concentration of receptors specific to oestrogens. This is the case, in particular, with cancers of the breast, uterus, ovary and prostate. For example, 65% of breast cancers possess detectable levels of oestrogen receptors (from 5000 to 50,000 receptor molecules per cell).

A suitable radioactive isotope attached to the steroid permits specific destruction of the cancer cells. In addition, a suitable radioactive isotope enables the tumour to be visualised by radio imaging. In fact, these ligands constitute targeting agents for the actual active component, which is the radionuclide.

For intracellular binding sites such as hormone receptors, hormone analogues possessing a high affinity for the receptor and a low affinity for the binding proteins in the plasma will be the most suitable targeting agents.

An object of the present invention was, in particular, to provide rhenium and technetium complexes possessing a high affinity for the oestrogen receptor and good stability, in particular for the purpose of labelling these complexes with a radioactive isotope of these metals for the applications mentioned above.

The subject of the present invention is, in effect, an organometallic oestrogen complex corresponding to the formula (I):

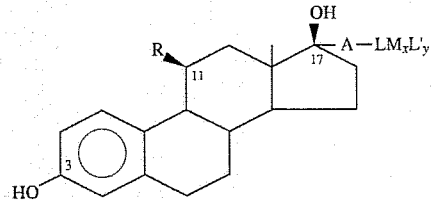

in which

A represents a $C_1$ to $C_7$ alkylene radical or a $C_2$ to $C_7$ alkenylene or alkynylene radical $M_x$ represents one or more identical or different transition metals $L'_y$ represents one or more identical or different ligands complexing the said metal(s) $M_x$ L represents a ligand for $M_x$ coupled covalently with A, or L represents "nothing" and $M_x$ is grafted directly onto a carbon of a C≡C triple bond of A, which represents an alkynylene radical, and R represents H, or a $C_1$ to $C_7$ alkyl or alkoxy optionally substituted, in particular, with one or more halogen(s); in particular, R can represent $CH_2Cl$, —$OCH_3$ or —$(CH_2)_nCH_3$ with n=1 to 4.

The hydroxyl functions at positions C-3 and C-17 endow these ligands with a high affinity for the oestrogen receptors.

The 11beta-chloromethyl function, where appropriate, enhances the stability of the receptor-hormone complex, thereby increasing its concentration in proximity to the cell nucleus. This function at the 11-beta-position effects in fact, a virtually irreversible binding to the oestrogen receptor.

These complexes satisfy the conditions required for their use, namely stability and good recognition by the oestradiol receptor.

An improvement in the affinity of the steroid complexes for the oestrogen receptor is observed when the metal complex $LM_xL'_y$ is separated from ring D by the linker A. In particular, there is a recognised improvement in the affinity of steroid-cyclopentadienyl-$Re(CO)_3$ complexes for the oestrogen receptor when the cyclopentadienyl is separated from ring D by a linker, especially a $CH_2$ group or an ethynylene group. The affinity of steroid-cyclopentadienyl-$Re(CO)_3$ derivatives grafted directly on ring D at the 17alpha-position is poor.

Among suitable metals of the organometallic compound according to the invention, metals chosen from Groups VI, VII, VIII and IX of the Periodic Classification of the elements may be mentioned.

Among the ligands $L'_y$ of these organometallic compounds, CO, CS, CSe, $CNR_1$, phenyl, $P(R_2R_3,R_4)$, cyclopentadienyl (Cp) may be mentioned as an example, $R_1$ being, in particular, an alkyl radical or —$COR_5$ and $R_2$, $R_3$, $R_4$ and $R_5$ being, in particular, substituted or unsubstituted phenyl or phenoxy radicals, substituted or unsubstituted $C_1$ to $C_7$ alkyl or alkoxy radicals or alternatively a halogen atom, it being possible for $R_5$ to be —$N(CH_2CH_2Cl)_2$.

The compounds $M_xL'_y$ can contain several metals, in particular two metals, and up to 12 ligands, in particular 3 to 7 ligands.

As has been seen, the metal $M_x$ preferably represents one or more atoms of a metal chosen from Re and Tc.

In particular, in the complexes according to the invention, A represents —$(CH_2)$— or —(C≡C)—. In this case, the complexes may be prepared by processes similar to those described in the examples which follow.

In the affinity labels of formula (I), L is preferably chosen from phenyl and cyclopentadienyl groups.

There may be mentioned, in particular, the complexes according to the invention in which:

$M_xL'_y$ is chosen from $Re(CO)_3$, $Re_2(CO)_7$, $Tc(CO)_3$ and $Tc_2(CO)_7$, in which case L is preferably coupled covalently to A and, as a further preference, L represents Cp or $C_6H_5$, or $M_xL'_y$ is chosen to be $Tc(CO)_5$ or $Re(CO)_5$, in which case L preferably represents "nothing", these organometallic complexes being grafted directly onto a carbon of a C≡C triple bond of A, which then represents an alkynylene radical.

The compounds according to the present invention may be prepared by known processes, in particular by the action of a corresponding organometallic derivative on the derivative of an oestrogen compound. Naturally, where necessary, some of the functions of the oestrogen compound may be protected, especially the hydroxyl at position 3, this likewise being done using known processes.

Thus, when A represents —C≡C—, it is possible to use the following reactions:

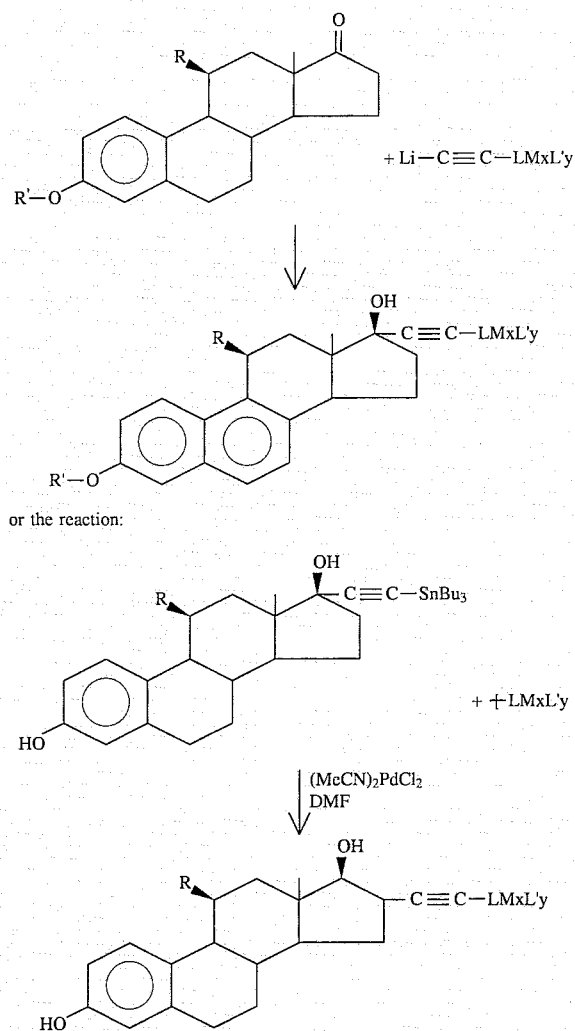

or the reaction:

This latter process makes it possible to gain a step in comparison to the one used previously. This gain in time is very important in the case where the radioactive label is involved.

When A represents —(CH$_2$)—$_n$, the following reaction may be used:

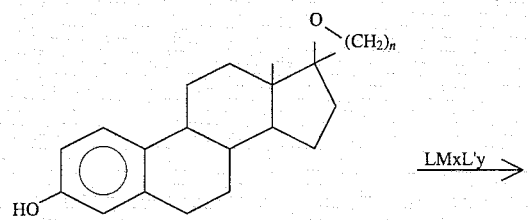

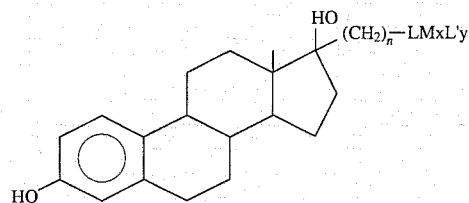

As has been stated, the complexes according to the invention may be used as medicinal products, in particular for hormone-dependent cancers, it being possible for the complexes according to the invention to be labelled or otherwise, or in medical imaging when they contain as metal a suitable radioactive isotope.

There may be mentioned, in particular, the complexes in which the metal is $^{186}$Re, $^{188}$Re or $^{99m}$Tc in medical imaging, and $^{186}$Re or $^{188}$Re in targeted in situ radiotherapy.

Other advantages and features of the present invention will become apparent in the light of the examples which follow.

EXAMPLE 1

17 alpha-Ethynylcyclopentadienylrhenium Derivative

This denotes the hormone complex of rhenium of formula (I)

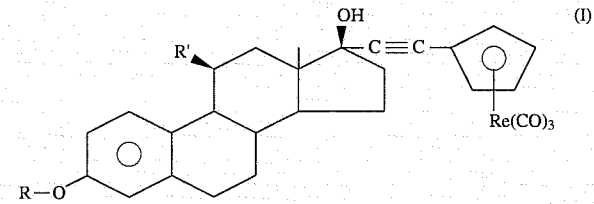

Hormone complex 1 R = H   R' = H
            2 R = PhCH$_2$  R' = H
            3 R = H   R' = ClCH$_2$ 1. Method of synthesis The following method of synthesis according to Scheme 1 below was adopted:

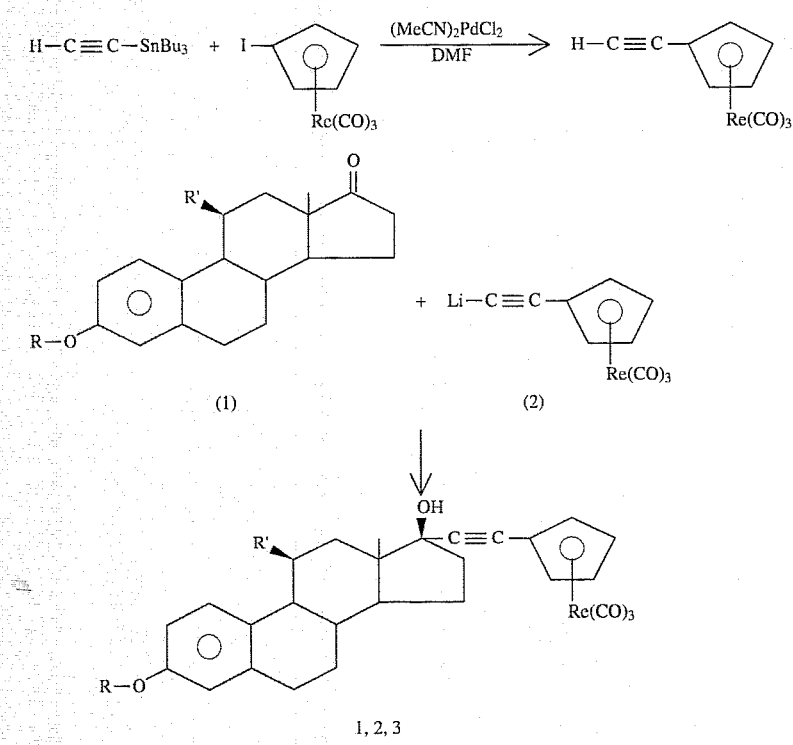

SCHEME 1

The hormone complexes may be obtained by reduction of the oestrone derivative (1) with the lithium derivative Li—C≡C—CpRe(CO)$_3$(2).

1. Synthesis of the compound H—C≡C—CpRe(CO)$_3$

The compound H—C≡C—CpRe(CO)$_3$ was prepared by Stille et al. according to the method of coupling between the tin derivative H—C≡C—SnBu$_3$ and the iodide ICpRe(CO)$_3$ (C. Lo Sterzo and J. K. Stille, Organometallics, 1990, 9, 687–694). The same method was followed for preparing this reactant.

H—C≡C—SnBu$_3$ is obtained by reaction between the acetylide H—C≡C—Li.EDA and the chloride ClSnBu$_3$. Coupling between H—C≡C—SnBu$_3$ and ICpRe(CO)$_3$ is then carried out in the presence of the catalyst (MeCN)$_2$PdCl$_2$.

2. Synthesis of the hormone complex 2

With the object of testing the feasability of the method, the oestrone (1) protected at position 3 with a benzyl group was first used. This protection enables the spurious reaction between the phenol function and the lithium derivative to be eliminated.

The lithium derivative Li—C≡C—CpRe(CO)$_3$ is first generated at −70° C. by the action of sec-BuLi on the compound H—C≡C—CpRe(CO)$_3$. The protected oestrone is then added to the solution of the lithium derivative maintained at −70° C. After the treatment and purification, the complex 2 is obtained in a 29% yield.

It is obviously possible to deprotect the hormone complex 2 to obtain the hormone; complex 1, but it is more practical to obtain this compound directly with oestrone.

3. Synthesis of the hormone complex 1

The direct use of oestrone in this type of reaction is handicapped by the reactivity of the phenol function and by its low solubility at low temperature. However, success was obtained in carrying out a direct reaction on oestrone by converting the phenol function beforehand to phenolate and diluting the reaction medium.

The hormone complex 1 is finally obtained in a 61% yield.

4. Synthesis of the hormone complex 3

11beta-Chloromethyl-beta-oestradiol possesses a very great advantage from the standpoint of affinity with respect to the oestradiol receptor. Its RBA value is very high, of the order of 1000. The 11beta-chloromethyl-beta-oestradiol complex may hence be expected to preserve a large RBA value also, The complex may be made according to the same procedure as that used for oestrone. In view of the difficulty of access to 11beta-chloromethyl-beta-oestradiol and its very high cost, it appears more shrewd to add the hormone directly to an excess of lithium derivative without prior conversion to a phenolate. In this situation, a portion of the lithium derivative Li—C≡C—CpRe(CO)$_3$ reacts with the phenol function., but this conversion does not represent a loss since regenerated H—C≡C—CpRe(CO)$_3$ is recoverable at the end of the reaction.

The hormone complex 3 is obtained in a very good yield of 78%.

It is hence possible to prepare hormone complexes of Re possessing good stability. The CpRe(CO)$_3$ group fulfils the conditions required for a label.

This labelling method is applicable to technetium labelling.

Generally speaking, rhenium and technetium compounds behave in the same way with respect to chemical reactions. This similarity enables reactions involving rhenium compounds to be transferred to the chemistry of technetium.

II. Experimental Part

1. H—C≡C—SnBu₃

The acetylide H—C≡C—Li is commercially available in the stabilised form H—C≡C—Li.EDA. We hence chose to use this reactant for the synthesis. 3.5 g (0.038 mol) of H—C≡C—Li.EDA are suspended in 40 mL of THF. A solution of ClSnBu₃ in THF (20 mL) is added dropwise to the first solution. Stirring is maintained overnight. After filtration and evaporation of the solvent, the oil obtained is subjected to a vacuum distillation. 4.3 g of H—C≡C—SnBu₃ are finally obtained in the form of a colourless oil, which distills at 70° C. at 0.1 mm Hg (literature 76° C./0.2 mm Hg; Nesmeyanov A. N. et al., Dokl. Akad. Nauk. SSSR, 1976, 174, 96), Yield: 36%. $^1$H NMR (200 MHz, CDCl₃, δ in ppm) 2.21 (s, 1H, CH), 0.92 (t, 9H, Me).

2. H—C≡C—CpRe(CO)₃

This is prepared according to the method described by Stille (C. Lo Sterzo and J. K. Stille, Organometallics, 1990, 9, 687–694).

$(\eta^5$—IC₅H₄)Re(CO)₃ (0.69 g, 1.5 mmol), H—C≡C—SnBu₃ (0.47 g, 1.5 mmol) and (MeCN)₂PdCl₂ (0.01 g, 0.02 mmol) are dissolved in 15 mL of DMF. After overnight stirring, 20 mL of ether and 10 mL of 50% aqueous KF solution are added. The mixture is stirred vigorously for 1 h while a stream of argon is passed through it at the same time. It is then poured into a separating funnel. The product is extracted first with 50 mL of ether. The ethereal solution is washed with water (twice). The aqueous wash is combined with the previous aqueous phase and the product is extracted again with ether (twice). The ether fractions are then combined together and washed with water. After drying over MgSO₄, filtration and evaporation, a solid is obtained, which solid is chromatographed on silica gel plates with the following as eluent: CH₂Cl₂/pentane, 1:10. The compound H—C≡C—CpRe(CO)₃ is finally obtained in the form of a beige solid, 0.40 g, 73% yld. $^1$H NMR (200 MHz, CDCl₃, δ in ppm) 2.83 (s, 1H, CH), 5.67 (t, 2H, Cp, J=2.3 Hz), 5.30 (t, 2H, Cp, J=2.3 Hz). IR (CH₂Cl₂) $\nu_{CO}$: 2028 S, 1932 S. This compound is identified by comparison of the IR and NMR data with those of the literature (Stille).

3. Hormone complex 2

0.216 g (0.6 mmol) of H—C≡C—CpRe(CO)₃ is dissolved in 4 mL of THF. After the solution has been cooled to −70° C., 0.77 mL of a 1.3M solution of sec-BuLi (1 mmol) is added to the above solution. The mixture is stirred at −70° C. for 20 min. A THF solution (3 mL) of 3-benzyloxy oestrone (0.216 g, 0,6 mmol) is then added dropwise. The addition takes ½ h. Stirring is maintained overnight while the temperature is allowed to rise slowly to room temperature ( 15 h). After hydrolysis, ether extraction and evaporation of the solvent, the crude product obtained is chromatographed on silica gel plates, eluent: ether/pentane, 1:2. 0.070 g of unreacted H—C≡C—CpRe(CO)₃ is recovered first, followed by 0.120 g of hormone complex 2 in the form of a beige oil which solidifies in pentane. The yield is 29%, or 42% taking account of the H—C≡C—CpRe(CO)₃. $^1$H NMR (200 MHz, CD₃COCD₃, δ in ppm) 7.40 (m, 5H, Ph), 7.19 (d, 1H, H-1, J=8.4 Hz), 6.77 (dd, 1H, H-2, J=8.4 and 2.8 Hz), 6.71 (d, 1H, H-4, J=2.8 Hz), 5.90 (t, 2H, Cp, J=2.2 Hz), 5.59 (t, 2H, Cp, J=2.2 Hz), 5.07 (s, 2H, CH₂-Ph), 4.49 (s, 1H, OH-17), 2.80 (m, 2H, H-6), 0.91 (s, 3H, Me-13). IR (CH₂Cl₂) $\nu_{CO}$: 2025 S, 1930 S. Mass (EI 70 eV), m/z 720 [M]⁺, 692 [M-CO]⁺, 636[M-3CO]⁺.

4. Hormone complex 1

0.216 g (0.6 mmol) of H—C≡C—CpRe(CO)₃ is dissolved in 4 mL of THF. After cooling to −50° C., 0.77 mL of a 1.3M solution of sec-BuLi (1 mmol) is added to the above solution. Stirring continues for 1 h. In another Schlenk tube 0.270 g (1 mmol) of oestrone is dissolved in 10 mL of THF. The solution is cooled to −50° C. and 0.77 mL of sec-BuLi (1 mmol) is added. The solution remains clear and colourless. This solution is then added slowly to the first solution maintained at −50° C. (1 h). The subsequent procedure is identical to that for the complex 2. After purification on plates (eluent:ether/pentane, 1:1), the complex 1 is obtained in the form of a colourless solid, 0.225 g, yld=61%. M.p. 161° C. (ether/pentane). $^1$H NMR (250 MHz, CD₂Cl₂, δ in ppm) 7.14 (d, 1H, H-1, J=8.4 Hz), 6.61 (dd, 1H, H-2, J=8.4 and 2.1 Hz), 6.55 (d, 1H, H-4, J=2.1 Hz), 5.71 (s, 1H, OH-3), 5.63 (t, 2H, Cp, J=2.2 Hz), 5.32 (t, 2H, Cp, J=2.2 Hz), 2.78 (m, 2H, H-6), 0.89 (s, 3H, Me-13). $^{13}$C NMR (62.89 MHz, CD₂Cl₂, δ in ppm) 193.29 (CO), 153.23 (C3), 137.92 (C5), 132.07 (C10), 126.06 (C1), 114.80 (C4), 12.27 (C2), 92.71 (C17), 87.52, 87.45, 84.04 and 83.95 (4C of Cp), 85.49 and 79.84 (1C of Cp and C≡), 76.54 (C≡), 49.31 (C14), 47.46 (C13), 43.07 (C9), 39.12 (C8), 38.52 (C16) 32.64 (C12), 29.24 (C6), 26.75 (C7), 26.11 (C11), 22.42 (C15), 12.31 (Me-13). IR (CH₂Cl₂) $\nu_{CO}$: 2025 S, 1930 S. Mass (EI 70 eV) m/z 630 [M]⁺, 612 [M-H₂O]⁺, 602 [M-CO]⁺, 546 [M-3CO]⁺.

5. Hormone complex 3

The procedure is identical to that for the complex 1.

In this case, an excess of Li—C≡C—CpRe(CO)₃ is used to neutralise the phenol function in situ. 11β-(Chloromethyl)Oestrone: 0.064 g, 0.2 mmol (10 mL THF); H—C≡C—CpRe(CO)₃: 0.216 g, 0.6 mmol (8 mL THF); sec-BuLi: 0.54 mL, 0.7 mmol (1.3M). The reaction is carried out at −60° C.

After overnight reaction, 20 mL of THF and 0.5 mL of water are added. The mixture is then filtered through silica gel and the solvent is evaporated off. In view of the low solubility of the product formed in ether or dichloromethane, this process enables the problem of extraction of the product from the aqueous phase to be eliminated. The crude product obtained is then chromatographed on silica gel plates with THF/pentane, 1:3 as eluent. The complex 3 is finally isolated in the form of a colourless solid, 0.105 g, 78% yld. M.p. 219° C. $^1$H NMR (250 MHz, CD₃COCD₃, δ in ppm) 8.17 (s, 1H, OH-3), 7.06 (d, 1H, H-1, J=8.5 Hz), 6.67 (dd, 1H H-2, J=8.2 and 2.7 Hz), 6.14 (d, 1H, H-4, J=2.7 Hz), 5.94 (t 2H, Cp, J=2.2 Hz), 5.59 (t, 2H, Cp, J=2.2 Hz), 4.63 (s, 1H, OH-17), 3.57 (m, 2H, CH₂Cl), 2.70 (m, 2H, H-6), 1.08 (s, 3H, Me-13), IR(CH₂Cl₂)$\nu_{CO}$: 2025S, 1930S. Mass (EI, 70 eV) m/z 678 (M)⁺, 650 (M-CO)⁺. 0.145 g of H—C≡C—CpRe(CO)₃ and 0.007 g of 11beta-(chloromethyl)oestrone are also recovered.

EXAMPLE 2

These complexes are of very great interest from the standpoint of labels, both for assay of receptors and for imaging. However, the use in imaging necessitates brevity in carrying Out the labelling. The reaction below can also be carried out by the following process:

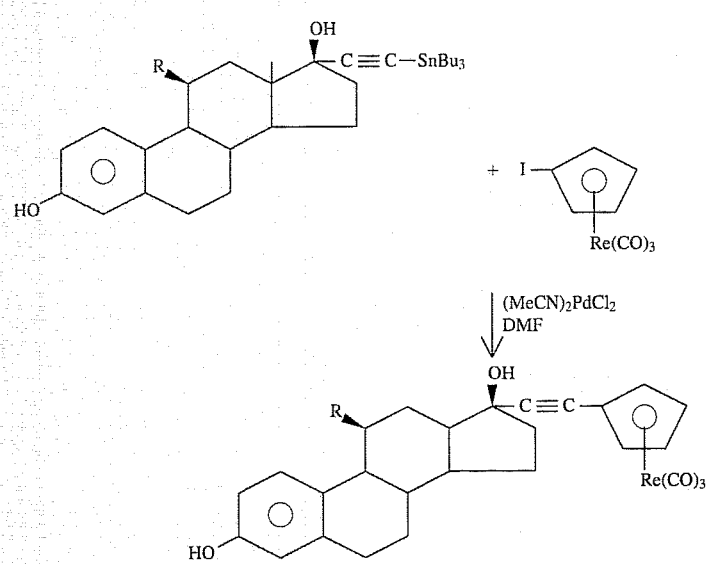

This procedure makes it possible to gain a step in comparison to that used in the previous cases. This gain in time is very important in the case of the radioactive label.

EXAMPLE 3

Methodology of the Biological Tests Performed and Results

The relative binding affinity (RBA) values were determined at temperatures (0° and 25° C.) according to the following protocol: Cytosol fractions (105,000 g supernatant) of ewes uterus are incubated (3 h at 0° C.; 3 h 30 min at 25° C.) in the presence of 2 nM tritiated oestradiol ($^3$H-E$_2$) and of increasing molarities of the test product (9 molarities between $10^{-9}$M and $10^{-8}$M). At the end of the incubation period, separation of the free and bound fractions of hormone is carried out by the protamine sulphate precipitation technique as described in the paper by A. Vessieres et al., Biochemistry 1988, 27, 6659. The RBA value, which is the ratio×100 of the concentration of non-radioactive oestradiol displacing 50% of the specific binding of oestradiol to its receptor to the molarity of modified hormone displacing 50% of this binding, is then determined. The higher the RBA value, the greater the affinity of the test hormone for the oestradiol receptor.

RESULTS

The three hormone complexes were subjected to measurement of the RNA value. The following values were found:

| Complex No. | Complex | RBA (%) (mean of 2 experiments) | |
|---|---|---|---|
| | | 0° C., 3 h | 25° C., 3 h 30 min |
| 2 | 17alpha-[—C≡C—CpRe(CO)$_3$]-3-benzyloxy-beta-oestradiol | 0 | not determined |
| 1 | 17alpha-[—C≡C—CpRe(CO)$_3$]-beta-oestradiol | 21 | 15 |

-continued

| Complex No. | Complex | RBA (%) (mean of 2 experiments) | |
|---|---|---|---|
| | | 0° C., 3 h | 25° C., 3 h 30 min |
| 3 | 17alpha-[—C≡C—CpRe(CO)$_3$]-11beta-chloromethyl-beta-oestradiol | 29 | 172 |

The complex 2 which does not possess a hydroxyl group at position 3 is not recognised by the receptor. For the rhenium complexes, there is a great difference in behaviour according to the temperature at which the test is carried out. At 0° C., the RBA values are very comparable for the complexes with or without 11beta-chloromethyl (complexes 3 and 1 respectively). In contrast, at 25° C., the RBA value of complex 1 decreases slightly whereas, for the complex 3, this value rises to 172%. This value indicates that the complex is recognised by the receptor better than oestradiol itself. It is the highest value ever found for an organometallic steroid.

EXAMPLE 4

17 alpha-Methylcycloentadienylrhenium Derivative

A method of synthesis is carried out according to Scheme 2 below:

SCHEME 2

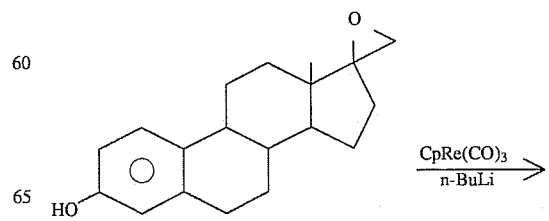

-continued
SCHEME 2

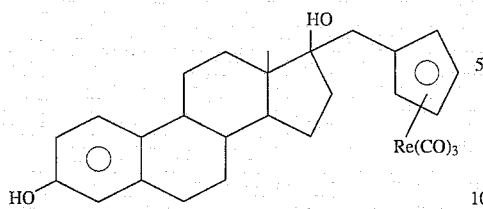

Butyllithium (1.6M in hexane; 0.33 ml) is added slowly to a solution, cooled to −78° C., of CpRe(CO)$_3$ (177 mg, 5.28×10$^{-6}$ mol) in anhydrous THF (5 ml). After stirring for one hour at −78° C., the epoxide 1 (50 mg, 1.76×10$^{-4}$ mol), dissolved in anhydrous THF (2 ml), is added. After 6 hours at room temperature, the reaction medium is hydrolysed with 10 ml of water, extracted with ether (5×10 ml), dried over MgSO$_4$ and then concentrated under reduced pressure. The product 2 is chromatographed on a plate, eluting with ether/pentane, 4:6, with a 65% yield.

EXAMPLE 5

Synthesis of Complexes in the Case Where L Represents a Direct Bond

In the case where L represents "nothing", M$_x$L'$_y$ can be Re(CO)$_5$. The grafting of these groups onto the hormone may be carried out according to the method adopted for the group CpM(CO)$_3$, that is to say reduction of the oestrone with the carbanion —C≡C—M(CO)$_5$. The latter may be obtained according to the following possibilities of synthesis, which are known to a person skilled in the art:

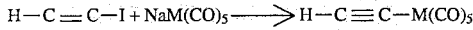

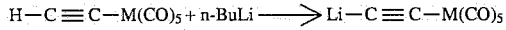

Or:

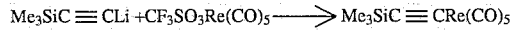

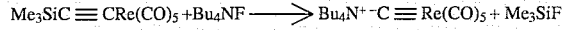

We claim:

1. An organometallic oestrogen complex of the formula (I):

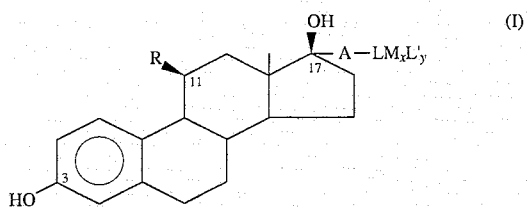

wherein

A represents a C$_1$ to C$_7$ alkylene radical or a C$_2$ to C$_7$ alkenylene or alkynylene radical, M$_2$ represents one or more identical or different transition metals, L'$_y$ represents one or more identical or different ligands complexing the metal(s) M$_x$ and L represents a ligand for M$_x$ coupled covalently to A selected from the group consisting of phenol and cyclopentadienyl, R represents H or a substituted or unsubstituted C$_1$ to C$_7$ alkyl or alkoxy.

2. The complex as claimed in claim 1 wherein R is a C$_1$ to C$_7$ alkyl or alkoxy which is substituted with one or more halogens.

3. The complex as claimed in claim 1 wherein M$_x$ represents one or more metal atom(s) selected from the group consisting of Re and Tc.

4. The complex as claimed in claim 3 wherein M$_x$L'$_y$ is selected from the group consisting of Re(CO)$_3$, Re$_2$(CO)$_7$, Tc(CO)$_3$ and Tc$_2$(CO)$_7$ and L represents cyclopentadienyl.

5. The complex as claimed in claim 1 wherein A represents —CH$_2$— or —C≡C—.

6. The complex as claimed in claim 1 wherein R represents H, CH$_2$Cl, —OCH$_3$, or —(CH$_2$)$_n$—CH$_3$ wherein n=1 to 4.

7. The complex as claimed in claim 6 wherein R is CH$_2$Cl.

8. A pharmaceutical composition comprising a complex as claimed in claim 1 and a pharmaceutically acceptable carrier.

9. The composition as claimed in claim 8 wherein the metal is rhenium.

10. The composition as claimed in claim 8 wherein the metal is a radioactive isotope selected from the group consisting of $^{186}$Re and $^{188}$Re.

11. A compound of claim 1 which is 17-α-ethynylcyclopentadienyl rhenium oestradiol.

12. An imaging agent comprising a complex according to claim 1 in which the metal is a radioactive isotope suitable for imaging.

13. The imaging agent as claimed in claim 12 wherein the metal is selected from the group consisting of $^{99m}$Tc, $^{186}$Re, and $^{188}$Re.

* * * * *

UNITED STATES PATENT AND TRADEMARK OFFICE
CERTIFICATE OF CORRECTION

PATENT NO. : 5,554,602
DATED      : September 10, 1996
INVENTOR(S) : Siden TOP et al.

It is certified that error appears in the above-indentified patent and that said Letters Patent is hereby corrected as shown below:

On the title page item [75], Inventors "G'erard JAQUEN" should read --Gérard JAOUEN--.

Signed and Sealed this

Eleventh Day of November, 1997

Attest:

BRUCE LEHMAN

*Attesting Officer*         *Commissioner of Patents and Trademarks*